United States Patent
Rapoport

(10) Patent No.: US 10,345,251 B2
(45) Date of Patent: Jul. 9, 2019

(54) PORTABLE NMR DEVICE FOR DETECTING AN OIL CONCENTRATION IN WATER

(71) Applicant: Aspect Imaging Ltd., Shoham (IL)

(72) Inventor: Uri Rapoport, Moshav Ben Shemen (IL)

(73) Assignee: ASPECT IMAGING LTD., Shoham (IL)

( * ) Notice: Subject to any disclaimer, the term of this patent is extended or adjusted under 35 U.S.C. 154(b) by 117 days.

(21) Appl. No.: 15/440,606

(22) Filed: Feb. 23, 2017

(65) Prior Publication Data

US 2018/0238819 A1    Aug. 23, 2018

(51) Int. Cl.
  *G01N 24/08* (2006.01)
  *G01N 33/18* (2006.01)
  *G01R 33/30* (2006.01)
  *G01R 33/421* (2006.01)

(52) U.S. Cl.
  CPC ........... *G01N 24/082* (2013.01); *G01N 33/18* (2013.01); *G01N 33/1833* (2013.01); *G01R 33/307* (2013.01); *G01R 33/421* (2013.01)

(58) Field of Classification Search
  USPC ................. 324/300–322; 600/407–435; 382/128–131
  See application file for complete search history.

(56) References Cited

U.S. PATENT DOCUMENTS

| 238,631 A | 3/1881 | Ball |
| 406,968 A | 7/1889 | Tesla |
| 2,239,144 A | 4/1941 | Dean et al. |
| 2,323,837 A | 7/1943 | Neal |
| 3,243,238 A | 3/1966 | Lyman |
| 3,512,852 A | 5/1970 | North |
| 3,815,963 A | 6/1974 | Wilk |
| 3,888,553 A | 6/1975 | Wehde |

(Continued)

FOREIGN PATENT DOCUMENTS

| CN | 1318503 | 10/2001 |
| CN | 103411991 | 11/2013 |

(Continued)

OTHER PUBLICATIONS

Berry et al., Of flying frogs and levitrons, Eur. J. Phys. 1997, 18, 307-313.

(Continued)

*Primary Examiner* — Melissa J Koval
*Assistant Examiner* — Tiffany A Fetzner
(74) *Attorney, Agent, or Firm* — Pearl Cohen Zedek Latzer Baratz LLP

(57) ABSTRACT

A portable nuclear magnetic resonance (NMR) device and a method of determining an oil concentration in water are disclosed. The portable NMR device can include a magnetic field assembly to carry out NMR measurements of water. The portable NMR device can include a housing to at least partly surround the magnetic field assembly and to substantially eliminate a magnetic fringe field generated by the magnetic field assembly outside the housing. The portable NMR device can also include an analysis module to receive the NMR measurement of the water and to determine, based on the received NMR measurements of the water, the oil concentration in the water.

13 Claims, 3 Drawing Sheets

(56) References Cited

U.S. PATENT DOCUMENTS

| | | |
|---|---|---|
| 4,222,021 A | 9/1980 | Bunker, Jr. |
| 4,379,598 A | 4/1983 | Goldowsky |
| 4,382,245 A | 5/1983 | Harrigan |
| 4,492,875 A | 1/1985 | Rowe |
| 4,514,691 A | 4/1985 | De Los Santos et al. |
| 4,517,514 A | 5/1985 | Howell |
| 4,585,282 A | 4/1986 | Bosley |
| 4,761,579 A | 8/1988 | Delassus |
| 4,785,245 A | 11/1988 | Lew et al. |
| 4,933,638 A | 6/1990 | Kenyon et al. |
| 5,168,226 A | 12/1992 | Hinks |
| 5,268,640 A | 12/1993 | Du et al. |
| 5,371,464 A | 12/1994 | Rapoport |
| 5,410,199 A | 4/1995 | Kinugasa et al. |
| 5,450,010 A | 9/1995 | Van Der Meulen et al. |
| 5,479,925 A | 1/1996 | Dumoulin et al. |
| 5,490,513 A | 2/1996 | Damadian et al. |
| 5,497,087 A | 3/1996 | Vinegar et al. |
| 5,498,960 A | 3/1996 | Vinegar et al. |
| 5,506,558 A | 4/1996 | Laube |
| 5,519,319 A | 5/1996 | Smith et al. |
| 5,532,593 A | 7/1996 | Maneval et al. |
| 5,596,275 A | 1/1997 | Dechene et al. |
| 5,675,253 A | 10/1997 | Smith et al. |
| 5,685,300 A | 11/1997 | Kuenstner |
| 5,705,928 A | 1/1998 | Haner et al. |
| 5,744,957 A | 4/1998 | Vaughan, Jr. |
| 5,838,155 A | 11/1998 | Bowers |
| 6,175,175 B1 | 1/2001 | Hull |
| 6,232,671 B1 | 5/2001 | Gottfried, Jr. |
| 6,278,891 B1 | 8/2001 | Reiderman et al. |
| 6,302,579 B1 | 10/2001 | Meyer et al. |
| 6,333,629 B1 | 12/2001 | Pykett et al. |
| 6,351,049 B1 | 2/2002 | Chassoulier et al. |
| 6,375,996 B1 | 4/2002 | Suter et al. |
| 6,380,737 B1 | 4/2002 | Myles |
| 6,522,145 B1 | 2/2003 | Damadian et al. |
| 6,549,007 B1 | 4/2003 | Hills et al. |
| 6,549,799 B2 | 4/2003 | Bock et al. |
| 6,563,315 B1 | 5/2003 | Boskamp et al. |
| 6,570,382 B1 | 5/2003 | Hurlimann et al. |
| 6,643,799 B1 | 11/2003 | Bonissone et al. |
| 6,668,403 B2 | 12/2003 | Seufert |
| 6,737,864 B2 | 5/2004 | Prammer et al. |
| 6,771,069 B2 | 8/2004 | Asano et al. |
| 6,859,033 B2 | 2/2005 | Speier |
| 6,879,076 B2 | 4/2005 | Long |
| 6,883,702 B2 | 4/2005 | Hurlimann et al. |
| 6,898,970 B2 | 5/2005 | Berstis |
| 6,972,565 B2 | 12/2005 | Yokoi et al. |
| 7,023,122 B2 | 4/2006 | Gang |
| 7,034,528 B2 | 4/2006 | Minh et al. |
| 7,053,611 B2 | 5/2006 | Freedman |
| 7,057,156 B2 | 6/2006 | Coates et al. |
| 7,084,627 B2 | 8/2006 | McKendry et al. |
| 7,127,499 B1 | 10/2006 | Accardi et al. |
| 7,345,478 B2 | 3/2008 | Lieblich et al. |
| 7,355,402 B1 | 4/2008 | Taicher et al. |
| 7,388,374 B2 | 6/2008 | Minh et al. |
| 7,394,183 B2 | 7/2008 | Ramer |
| 7,397,241 B2 | 7/2008 | Gauthausen et al. |
| 7,400,147 B2 | 7/2008 | Rapoport |
| 7,501,922 B2 | 3/2009 | Kazadi |
| 7,511,487 B2 | 3/2009 | Badry et al. |
| 7,764,064 B2 | 7/2010 | Reiss et al. |
| 7,880,467 B2 | 2/2011 | Rapoport |
| 8,185,315 B2 | 5/2012 | Coope et al. |
| 8,427,145 B2 | 4/2013 | Mitchell et al. |
| 8,519,708 B2 * | 8/2013 | Prado .................. G01N 24/08 324/309 |
| 8,686,724 B2 | 4/2014 | Mitchell et al. |
| 8,766,631 B2 | 7/2014 | Hofmann et al. |
| 8,807,084 B2 | 8/2014 | Rapoport et al. |
| 8,820,226 B2 | 9/2014 | Milla et al. |
| 8,851,018 B2 | 10/2014 | Rapoport et al. |
| 8,896,310 B2 | 11/2014 | Rapoport |
| 8,917,918 B2 * | 12/2014 | Jellus ............... G01R 33/56527 378/1 |
| 9,006,914 B2 | 4/2015 | Rapoport |
| 9,617,831 B2 * | 4/2017 | Jones .................. E21B 43/28 |
| 2002/0030491 A1 | 3/2002 | Kose |
| 2002/0048610 A1 | 4/2002 | Cima et al. |
| 2003/0169040 A1 | 9/2003 | Hurlimann et al. |
| 2003/0178994 A1 | 9/2003 | Hurlimann et al. |
| 2003/0197433 A1 | 10/2003 | Cheung et al. |
| 2004/0058559 A1 | 3/2004 | Govindarajan et al. |
| 2004/0090231 A1 | 5/2004 | Augustine et al. |
| 2004/0140875 A1 | 7/2004 | Strom |
| 2004/0164735 A1 | 8/2004 | Hurlimann et al. |
| 2004/0169511 A1 | 9/2004 | Minh et al. |
| 2004/0169512 A1 | 9/2004 | Jara |
| 2005/0270023 A1 | 12/2005 | Freedman |
| 2006/0001323 A1 | 1/2006 | Gang |
| 2007/0096603 A1 | 5/2007 | Ramer |
| 2009/0115416 A1 | 5/2009 | White et al. |
| 2009/0167033 A1 | 7/2009 | Rapoport |
| 2009/0167322 A1 | 7/2009 | Magnuson et al. |
| 2010/0237860 A1 | 9/2010 | Hurlimann et al. |
| 2010/0288093 A1 | 11/2010 | Seager et al. |
| 2011/0162652 A1 | 7/2011 | Rapoport |
| 2011/0186049 A1 | 8/2011 | Rapoport |
| 2011/0234220 A1 | 9/2011 | Mitchell et al. |
| 2011/0234347 A1 | 9/2011 | Rapoport |
| 2011/0304333 A1 | 12/2011 | Rapoport |
| 2012/0062226 A1 | 3/2012 | Pielak et al. |
| 2012/0071745 A1 | 3/2012 | Rapoport |
| 2012/0073511 A1 | 3/2012 | Rapoport et al. |
| 2012/0077707 A1 | 3/2012 | Rapoport |
| 2012/0119742 A1 | 5/2012 | Rapoport |
| 2012/0169069 A1 | 7/2012 | Rapoport |
| 2013/0057277 A1 | 3/2013 | Zielinski et al. |
| 2013/0079624 A1 | 3/2013 | Rapoport |
| 2013/0109956 A1 | 5/2013 | Rapoport |
| 2013/0230223 A1 * | 9/2013 | Jellus .................. A61B 5/00 382/131 |
| 2013/0237803 A1 | 9/2013 | Rapoport |
| 2013/0265055 A1 | 10/2013 | Mitchell et al. |
| 2013/0328559 A1 | 12/2013 | Rapoport |
| 2013/0328560 A1 | 12/2013 | Rapoport |
| 2013/0328563 A1 | 12/2013 | Rapoport |
| 2014/0050824 A1 | 2/2014 | Rapoport |
| 2014/0050827 A1 | 2/2014 | Rapoport |
| 2014/0051973 A1 | 2/2014 | Rapoport et al. |
| 2014/0051974 A1 | 2/2014 | Rapoport et al. |
| 2014/0051976 A1 | 2/2014 | Rapoport et al. |
| 2014/0099010 A1 | 4/2014 | Rapoport |
| 2014/0103927 A1 | 4/2014 | Rapoport |
| 2014/0117989 A1 | 5/2014 | Rapoport |
| 2014/0128725 A1 | 5/2014 | Rapoport |
| 2014/0139216 A1 | 5/2014 | Rapoport |
| 2014/0142914 A1 | 5/2014 | Rapoport |
| 2014/0152302 A1 | 6/2014 | Rapoport et al. |
| 2014/0152310 A1 | 6/2014 | Rapoport |
| 2014/0158062 A1 | 6/2014 | Rapoport et al. |
| 2014/0167756 A1 | 6/2014 | Cho et al. |
| 2014/0230850 A1 | 8/2014 | Rapoport |
| 2014/0257081 A1 | 9/2014 | Rapoport |
| 2014/0266203 A1 | 9/2014 | Rapoport |
| 2014/0285196 A1 | 9/2014 | Liu et al. |
| 2014/0300358 A1 | 10/2014 | Rapoport |
| 2014/0320126 A1 | 10/2014 | Heaton et al. |
| 2014/0378821 A1 | 12/2014 | Rapoport et al. |
| 2014/0378825 A1 | 12/2014 | Rapoport et al. |
| 2015/0059157 A1 | 3/2015 | Rapoport |
| 2015/0059655 A1 | 3/2015 | Rapoport |
| 2015/0065788 A1 | 3/2015 | Rapoport |
| 2015/0073204 A1 | 3/2015 | Rapoport |
| 2015/0084630 A1 | 3/2015 | Rapoport |
| 2015/0087051 A1 | 3/2015 | Rapoport |
| 2015/0112186 A1 | 4/2015 | Rapoport et al. |
| 2015/0126804 A1 | 5/2015 | Rapoport |
| 2015/0130460 A1 | 5/2015 | Valori et al. |
| 2015/0137812 A1 | 5/2015 | Rapoport |
| 2015/0141799 A1 | 5/2015 | Rapoport et al. |

(56) References Cited

U.S. PATENT DOCUMENTS

| | | | |
|---|---|---|---|
| 2015/0159471 A1* | 6/2015 | Jones | E21B 43/28 |
| | | | 166/302 |
| 2015/0160311 A1 | 6/2015 | Rapoport et al. | |
| 2015/0168519 A1 | 6/2015 | Rapoport | |
| 2015/0231012 A1 | 8/2015 | Rapoport | |
| 2015/0253397 A1 | 9/2015 | Rapoport | |
| 2015/0253400 A1 | 9/2015 | Rapoport | |
| 2015/0253401 A1 | 9/2015 | Rapoport | |
| 2015/0253454 A1 | 9/2015 | Song et al. | |
| 2016/0011290 A1* | 1/2016 | Iannello | A61B 5/055 |
| | | | 600/309 |
| 2016/0077171 A1 | 3/2016 | Rabinovitz et al. | |
| 2016/0077176 A1 | 3/2016 | Rabinovitz et al. | |
| 2016/0116540 A1 | 4/2016 | Zheng et al. | |
| 2018/0058180 A1* | 3/2018 | Jones | E21B 43/28 |
| 2018/0238819 A1* | 8/2018 | Rapoport | G01N 33/18 |

FOREIGN PATENT DOCUMENTS

| | | |
|---|---|---|
| DE | 102010021260 | 11/2011 |
| EP | 0584112 | 11/1999 |
| EP | 1253433 | 10/2002 |
| EP | 2345330 | 7/2011 |
| EP | 2732046 | 1/2013 |
| GB | 2120075 | 11/1983 |
| GB | 2397698 | 7/2004 |
| JP | 2110358 | 4/1990 |
| JP | 07-198636 | 8/1995 |
| JP | 2558727 | 9/1996 |
| JP | 09-297113 | 11/1997 |
| JP | 11-142354 | 5/1999 |
| JP | 2002501204 | 1/2002 |
| JP | 2002122418 | 4/2002 |
| JP | 2006149164 | 6/2006 |
| JP | 2007100124 | 4/2007 |
| RU | 2177201 | 12/2001 |
| WO | WO2004104989 | 12/2004 |
| WO | WO2007144873 | 12/2007 |
| WO | WO2008016309 | 2/2008 |
| WO | WO2013010080 | 1/2013 |

OTHER PUBLICATIONS

Coates, John, Think small: low-cost optical spectral measurements for chemical sensing, Spectroscopy, Spectroscopyonline.com, http://www.spectroscopyonline.com/think-small-low-cost-optical-spectral-measurements-chemical-sensing, 2006, vol. 21, Issue 10.

Ding et al., Advances in water cut metering with low field NMR, Department of Chemical and Petroleum Engineering, TIPM Laboratory, University of Calgary, 2004.

Dubois et al., NeSSI new sampling/sensor initiative generation II specification, Jun. 21, 2004, https://www.cpac.washington.edu/NeSSI/NeSSI.htm, 1-53.

Earnshaw's Theorem, Wikipedia, citation 2011, 1-6 http://en.wikpedia.org/wiki/Earnshaw%27s_theorem.

Gibbs et al., Is magnetic levitation possible?, Mar. 1997, 1-3 http://www.ru.nl/html/research/levitation/diamagnetic/levitation_possible/.

Hernandez-Sanchez et al., Detection of freeze injury in oranges by magnetic resonance imaging of moving samples, Appl. Magn. Reson. 2004, 26, 431-445.

IEC/PAS 62339-1, edition 1.0, Aug. 2003, ANSI/ISA-76.00.02-2002, Modular component interfaces for surface-mount fluid distribution components—part 1: elastomeric seals, 2002, 1-6.

Joliffe, I.T., Principal component analysis, second edition, Springer, 2002, 1-518.

Lucas et al., An iterative image registration technique with an application to stereo vision, Proceedings of imaging understanding workshop, 1981, 121-130.

Tea et al., H-NMR-based metabolic profiling of maternal and umbilical cord blood indicates altered materno-foetal nutrient exchange in preterm infants, PLOS ONE, 2012, vol. 7, Issue 1, e29947, 1-12.

Wright et al., NMR imaging of packaged foods, in book of M. Mathlouthi (ed.) Food Packaging and Preservation, Chapman & Hall, chapter 11, 1994, 197-209.

\* cited by examiner

PORTABLE NMR DEVICE FOR DETECTING AN OIL CONCENTRATION IN WATER

FIELD OF THE INVENTION

The present invention relates to the field of nuclear magnetic resonance devices, and more particularly, to detection of an oil in a water using nuclear magnetic resonance devices.

BACKGROUND OF THE INVENTION

Oil is commonly cleaned in an oil cleaning system which can receive cleaning water. The cleaning water can remove contaminants (e.g., salts) from the oil until, for example, the oil reaches a specified cleanliness level. The water exiting the oil cleaning system can include, for example, residuals of the oil. In order to be recycled, typically, a maximum amount of oil in the water (e.g., an amount in parts per million) can be specified (e.g., by a municipality, town, etc.) as an indicator of whether the water is recyclable or not.

SUMMARY OF THE INVENTION

One aspect of the present invention provides a portable nuclear magnetic resonance (NMR) device for detecting an oil concentration in water, the NMR device includes: a magnetic field assembly including at least one magnet and at least one radiofrequency (RF) coil, the magnetic field assembly to generate a magnetic field to carry out NMR measurements of water and to enable a detection of an oil in the water, wherein the oil concentration in the water is at least 50 parts per million (ppm); a housing to at least partly surround the magnetic field assembly and to substantially eliminate a magnetic fringe field generated by the magnetic field assembly outside the housing; and an analysis module to receive the NMR measurement of the water and to determine, based on the received NMR measurements of the water, the oil concentration in the water.

In some embodiments, the magnetic field assembly is coupled to an oil cleaning system.

In some embodiments, the magnetic field assembly to carry out NMR measurements of water exiting the oil cleaning system.

In some embodiments, the analysis module to determine, based on the NMR measurements, the oil concentration in the water exiting the oil cleaning system.

In some embodiments, the magnetic field assembly further to carry out NMR measurements of water exiting the oil cleaning system and to enable a detection of at least one oil contaminant in the water exiting the oil cleaning system.

In some embodiments, the analysis modulus further to determine, based on the NMR measurements, a concentration of the at least one oil contaminant in the water exiting the oil cleaning system and to indicate, based on the determined concentration, oil cleanliness.

In some embodiments, the magnetic field assembly further to carry out NMR measurements of water entering and water exiting the oil cleaning system and to enable a first detection of at least one oil contaminant in the water entering the oil cleaning system and a second detection of at least one oil contaminant in the water exiting the oil cleaning system.

In some embodiments, the analysis modulus further to compare, based on the NMR measurements, the first and second detections and to determine, based on the comparison, a lack of difference between the first and second detections to indicate, based on the lack of difference, oil cleanliness.

Another aspect of the present invention provides a method of detecting an oil concentration in water, the method includes: generating a magnetic field within a measurement volume to enable on-line and in-line detection of an oil in water, wherein the oil concentration in the water is at least 50 parts per million (ppm); carrying out nuclear magnetic resonance (NMR) measurements of the water to detect the oil in the water; determining, based on the NMR measurements, the oil concentration in the water; and shielding an environment external to the measurement volume to substantially eliminate a magnetic fringe field.

In some embodiments, the method further includes generating a magnetic field to enable a detection of at least one oil contaminant in the water.

In some embodiments, the method further includes carrying out NMR measurements to detect the at least one oil contaminant in the water.

In some embodiments, the method further includes determining, based on the NMR measurements, the concentration of the at least one oil contaminant in the water.

In some embodiments, the method further includes indicating, based on the determined concentration, oil cleanliness.

These, additional, and/or other aspects and/or advantages of the present invention are set forth in the detailed description which follows; possibly inferable from the detailed description; and/or learnable by practice of the present invention.

BRIEF DESCRIPTION OF THE DRAWINGS

For a better understanding of embodiments of the invention and to show how the same may be carried into effect, reference will now be made, purely by way of example, to the accompanying drawings in which like numerals designate corresponding elements or sections throughout.

In the accompanying drawings.

DETAILED DESCRIPTION OF THE INVENTION

Figure 1A:
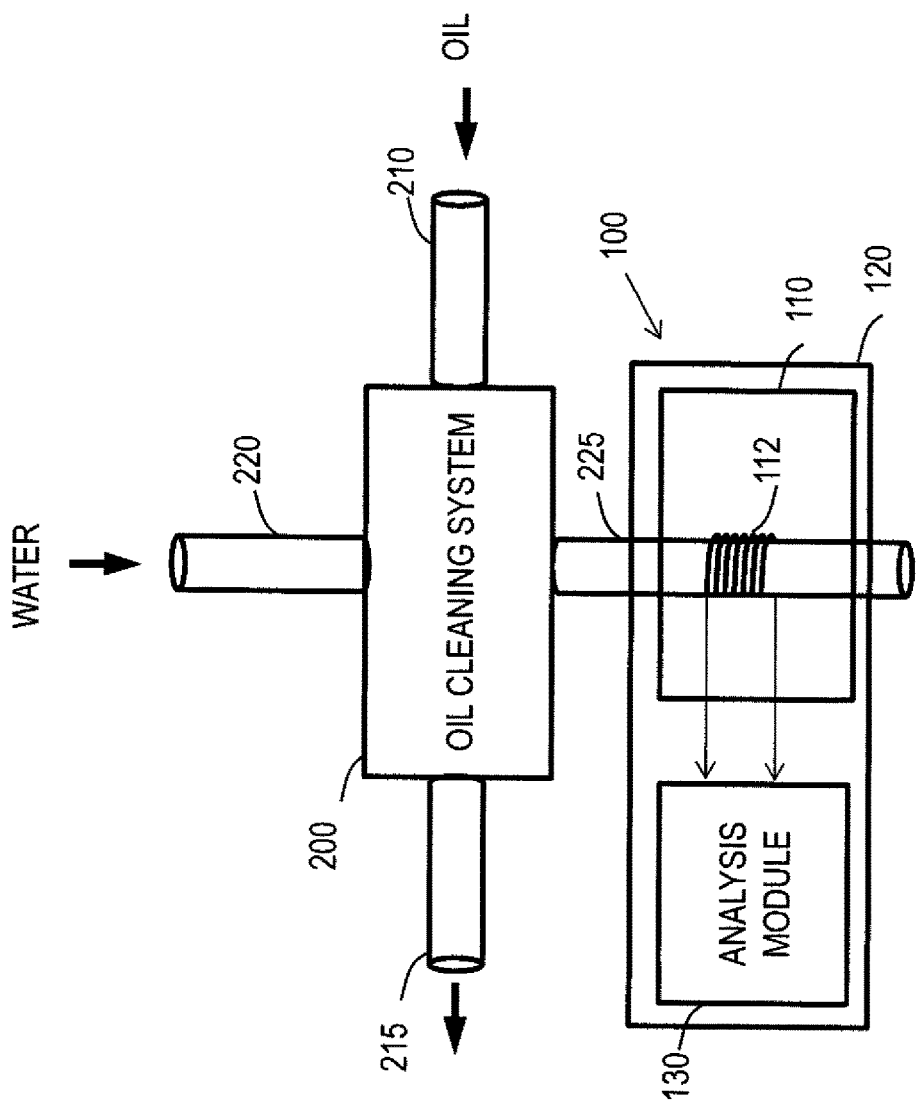
FIG. 1A is an illustration of a portable nuclear magnetic resonance (NMR) device coupled to a water outlet of an oil cleaning system, according to some embodiments of the invention.

In the following description, various aspects of the present invention are described. For purposes of explanation, specific configurations and details are set forth in order to provide a thorough understanding of the present invention. However, it will also be apparent to one skilled in the art that the present invention may be practiced without the specific details presented herein. Furthermore, well known features may have been omitted or simplified in order not to obscure the present invention. With specific reference to the drawings, it is stressed that the particulars shown are by way of example and for purposes of illustrative discussion of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

Before at least one embodiment of the invention is explained in detail, it is to be understood that the invention is not limited in its application to the details of construction and the arrangement of the components set forth in the following description or illustrated in the drawings. The invention is applicable to other embodiments that may be practiced or carried out in various ways as well as to combinations of the disclosed embodiments. Also, it is to be understood that the phraseology and terminology employed herein is for the purpose of description and should not be regarded as limiting.

Generally, the invention can include a portable nuclear magnetic resonance (NMR) device and/or a method of determining an oil concentration in water. The portable NMR device can include a magnetic field assembly to carry out NMR measurements of water. The portable NMR device can include a housing to at least partly surround the magnetic field assembly and/or to substantially eliminate a magnetic fringe field generated by the magnetic field assembly outside the housing. The portable NMR device can also include an analysis module to receive the NMR measurement of the water and to determine, based on the received NMR measurements of the water, the oil concentration in the water.

FIG. 1A is an illustration of a portable nuclear magnetic resonance (NMR) device 100 coupled to a water outlet 225 of an oil cleaning system 200, according to some embodiments of the invention.

A portable nuclear magnetic resonance (NMR) device 100 can include a magnetic field assembly 110. The magnetic field 110 assembly can include at least one magnet (not shown), for example a permanent magnet, and/or at least one radiofrequency (RF) coil 112. The magnetic field assembly 110 can generate, for example by the at least one magnet and/or RF coil 112, a magnetic field to carry out NMR measurements of water. The generated magnetic field can enable a detection of an oil in the water, where the oil concentration is at least 50 parts per million (ppm).

The portable NMR device 100 can include a housing 120 to at least partly surround the magnetic field assembly 110. The housing 120 can, for example, substantially eliminate a magnetic fringe field generated by the magnetic field assembly 110 outside the housing 120.

The portable NMR device 100 can also include an analysis modulus 130. The analysis modulus 130 can receive the NMR measurement of the water and/or determine, based on the received NMR measurements of the water, the oil concentration in the water.

The portable NMR device 100 can be coupled to an oil cleaning system 200, to, for example, detect an oil concentration in oil exiting the oil cleaning system 200. The oil cleaning system 200 can include at least one oil inlet 210 and/or at least one oil outlet 215. The oil cleaning system 200 can also include at least one water inlet 220 and/or at least one water outlet 225.

The oil cleaning system 200 can receive (e.g., through the oil inlet 210) an oil with oil contaminants (e.g., salts and/or chemicals) and/or to provide cleaned oil (e.g., through the oil outlet 215). The oil cleaning system 200 can remove the contaminants from the oil by cleaning it using cleaning water. The cleaning water can enter the oil cleaning system (e.g., through the water inlet 220) and/or can exit the cleaning system 200 (e.g., through the water outlet 225) as a water with the oil contaminants (e.g., salt and/or chemicals).

In some embodiments, the water exiting the oil cleaning system 200 also includes oil. A concentration of the oil in the water exiting the oil cleaning system 200 can be detected using the portable NMR system 100. For example, the RF coil 112 of the magnetic field assembly 110 of the portable NMR device 100 can be located along the water outlet 225 of the cleaning system 200. The RF coil 112 can transmit and/or receive RF signals to provide NMR measurements of the water exiting the oil cleaning system 200. The analysis modulus 130 of the portable NMR device 100 can receive the NNMR measurements and/or determine, based on the received NMR measurements, the oil concentration in the water exiting the oil cleaning system 200. In some embodiments, water exiting the oil cleaning system 200 with the oil concentration less than 50 parts per million (ppm) is recycled.

In some embodiments, the magnetic field assembly 110 of the portable NMR device 100 generates a magnetic field and/or RF signals that can enable a detection of the oil contaminants (e.g., salts and/or chemicals) in the water exiting the oil cleaning system 200. For example, the RF coil 112 (e.g., that can be located along the water outlet 225) can transmit and/or receive RF signals to provide NMR measurements of the water exiting the oil cleaning system 200. In various embodiments, the analysis modulus 130 receives the NMR measurements, determines, based on the received NMR measurements, a concentration of the at least one oil contaminant in the water exiting the oil cleaning system and/or indicates, based on the determined concentration, oil cleanliness.

Figure 1B:
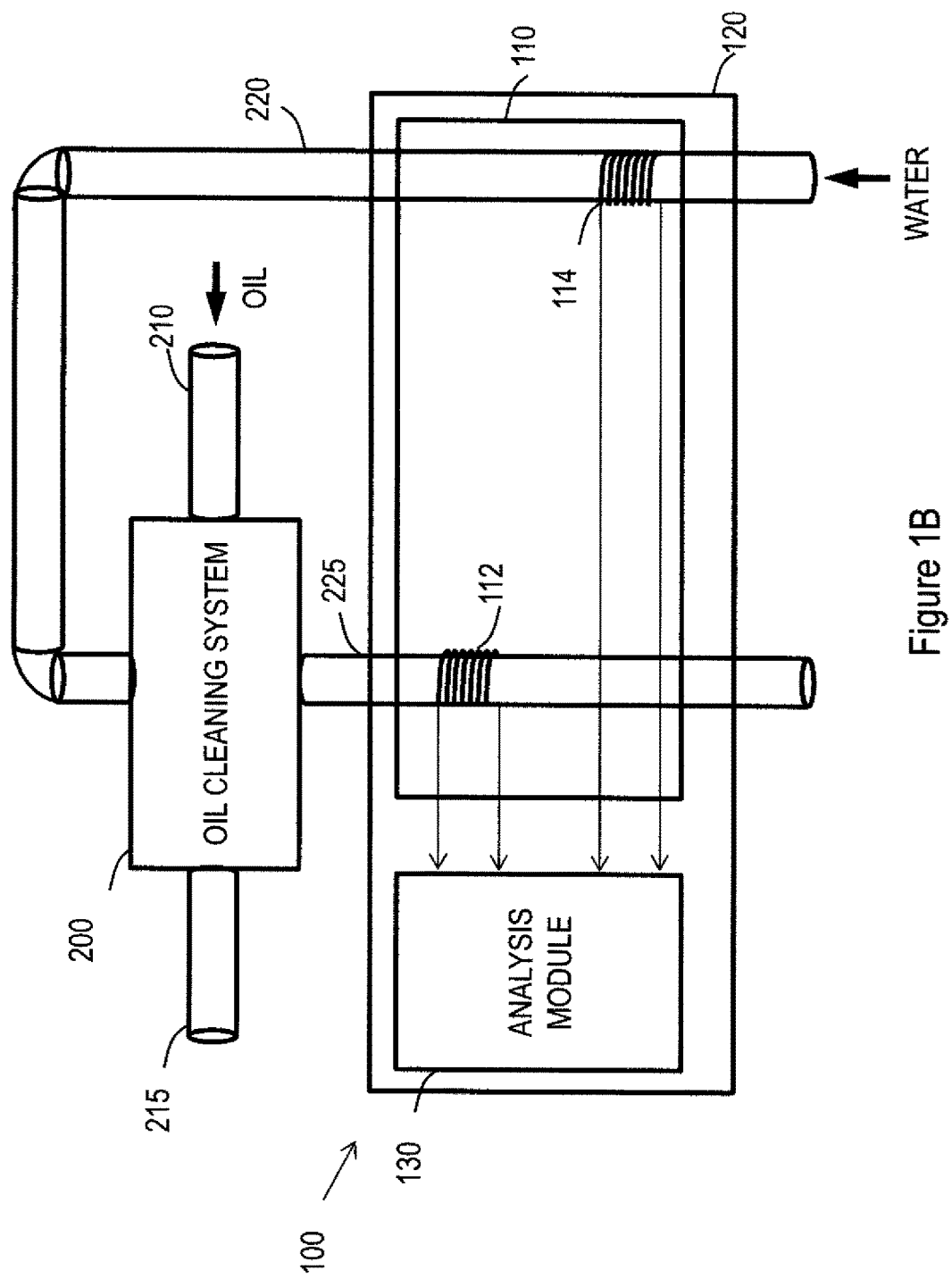
FIG. 1B is an illustration of a portable nuclear magnetic resonance (NMR) device coupled to a water inlet and a water outlet of an oil cleaning system, according to some embodiments of the invention.

FIG. 1B is an illustration of a portable nuclear magnetic resonance (NMR) device 100 coupled to a water inlet 220 and a water outlet 225 of an oil cleaning system 200, according to some embodiments of the invention.

The magnetic field assembly 110 of the portable NMR system 100 can include more than one RF coil 112. In various embodiments, magnetic field assembly 110 includes two RF coils 112, 114 located onto the water outlet 225 and/or water inlet 220 of the oil cleaning system 200, respectively (e.g., as shown in FIG. 1B). The RF coil 114 can transmit and/or receive RF signals to carry out NMR measurement of water entering the oil cleaning system 200 (e.g., through the water inlet 220) to enable a first detection of the oil contaminant in the entering water. The RF coil 112 can transmit and/or receive RF signals to carry out NMR measurements of water exiting the oil cleaning system (e.g., through the water outlet 225) to enable a second detection of the oil contaminants in the exiting water.

The analysis modulus 130 can receive the NMR measurements, determine, based on the received NMR measurements of the first and/or the second detections, a concentration of the oil contaminants in the entering and exiting water. The analysis modulus 130 can also compare the first and second detections, determine, based on the comparison, a lack of difference between the first and second detections and/or indicate, based on the lack of difference, oil cleanliness.

Figure 2:
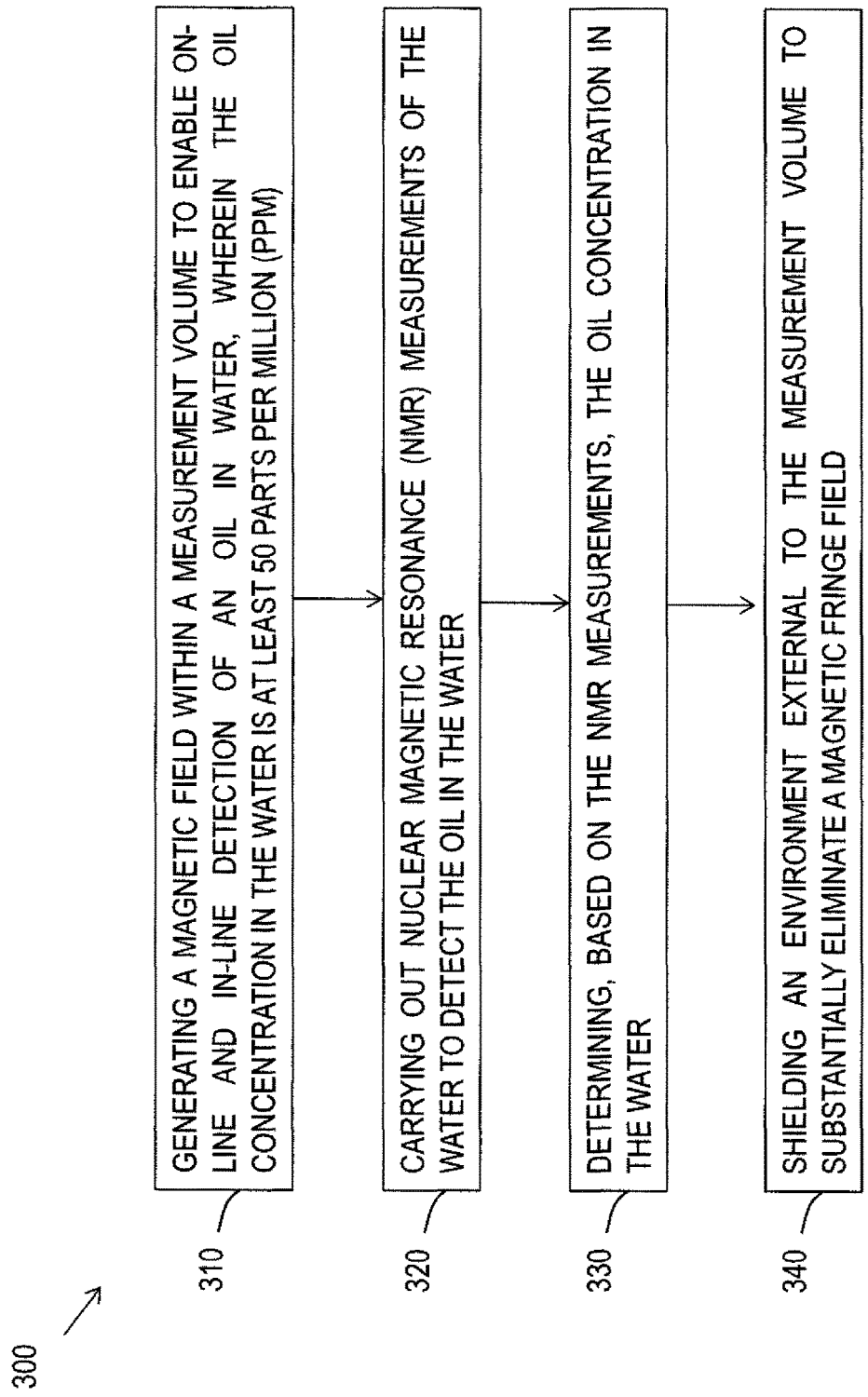
FIG. 2 is a flowchart illustrating a method of detecting an oil concentration in water, according to some embodiments of the invention.

FIG. 2 is a flowchart illustrating a method 300 of detecting an oil concentration in water, according to some embodiments of the invention.

The method 300 can include generating 310 a magnetic field (e.g., by the magnetic field assembly 110) within a measurement volume to, for example, enable on-line and/or in-line detection of an oil in water, where the oil concentration in the water is at least 50 parts per million (ppm). In some embodiments, the method 300 further includes generating a magnetic field to enable a detection of at least one oil contaminant (e.g., salt and/or chemicals) in the water.

The method 300 can include carrying out 320 nuclear magnetic resonance (NMR) measurements of the water (e.g., by the RF coil 112) to detect the oil in the water. In some embodiments, the method 300 further includes carrying out NMR measurements to detect the at least one oil contaminant in the water.

The method 300 can include determining 330 (e.g., by the analysis modulus 130), based on the NMR measurements, the oil concentration in the water. In some embodiments, the method 300 further includes determining, based on the NMR measurements, the concentration of the at least one oil contaminant in the water. In some embodiments, the method 300 further includes indicating, based on the determined concentration, oil cleanliness.

The method 300 can include shielding 340 (e.g., by the housing 120) an environment external to the measurement volume to substantially eliminate a magnetic fringe field.

In the above description, an embodiment is an example or implementation of the invention. The various appearances of "one embodiment", "an embodiment", "certain embodiments" or "some embodiments" do not necessarily all refer to the same embodiments. Although various features of the invention may be described in the context of a single embodiment, the features may also be provided separately or in any suitable combination. Conversely, although the invention may be described herein in the context of separate embodiments for clarity, the invention may also be implemented in a single embodiment. Certain embodiments of the invention may include features from different embodiments disclosed above, and certain embodiments may incorporate elements from other embodiments disclosed above. The disclosure of elements of the invention in the context of a specific embodiment is not to be taken as limiting their use in the specific embodiment alone. Furthermore, it is to be understood that the invention can be carried out or practiced in various ways and that the invention can be implemented in certain embodiments other than the ones outlined in the description above.

The invention is not limited to those diagrams or to the corresponding descriptions. For example, flow need not move through each illustrated box or state, or in exactly the same order as illustrated and described. Meanings of technical and scientific terms used herein are to be commonly understood as by one of ordinary skill in the art to which the invention belongs, unless otherwise defined. While the invention has been described with respect to a limited number of embodiments, these should not be construed as limitations on the scope of the invention, but rather as exemplifications of some of the preferred embodiments. Other possible variations, modifications, and applications are also within the scope of the invention. Accordingly, the scope of the invention should not be limited by what has thus far been described, but by the appended claims and their legal equivalents.

The invention claimed is:

1. A portable nuclear magnetic resonance (NMR) device configured for detecting an oil concentration in water, the portable NMR device comprising:

a magnetic field assembly comprising at least one magnet and at least one radiofrequency (RF) coil;

wherein the magnetic field assembly generates a magnetic field that is utilized in carrying out NMR measurements on water that passes through the portable NMR device; and wherein the NMR measurements enable a detection of an oil in the water, when the oil concentration in the water is at least 50 parts per million (ppm);

a housing partly surrounding the magnetic field assembly that substantially eliminates a magnetic fringe field generated by the magnetic field assembly from extending beyond the outside of the housing; and an analysis module that is configured in order to receive the carried out NMR measurements that are performed on the water and the analysis module being configured to determine, based on the received NMR measurements that are carried out on the water that passes through the portable NMR device, the oil concentration that is present in the water.

2. The portable NMR device of claim 1, wherein the magnetic field assembly connects and attaches to an oil cleaning system via coupling.

3. The portable NMR device of claim 2, wherein the magnetic field assembly is utilized in order to carry out NMR measurements on the water that is exiting the oil cleaning system which had been connected and attached via said coupling to the magnetic field assembly.

4. The portable NMR device of claim 3, wherein the analysis module determines based on the received NMR measurements, the oil concentration in the water exiting the oil cleaning system.

5. The portable NMR device of claim 2, wherein the magnetic field assembly is further configured to carry out NMR measurements on, and detect at least one contaminant within the water that is exiting the oil cleaning system which is connected and attached via said coupling to the magnetic field assembly.

6. The portable NMR device of claim 5, wherein the analysis modulus is further configured to determine, based on the carried out NMR measurements that are received by the analysis module, a concentration of the at least one oil contaminant, that was detected in the water exiting the oil cleaning system and wherein the analysis module is also utilized to indicate, based on the determined concentration of the at least one oil contaminant, an amount of oil cleanliness.

7. The portable NMR device of claim 2, wherein the magnetic field assembly is further configured to carry out NMR measurements on, and detect, by performing a first and second detection, at least one contaminant within, the water that is exiting the oil cleaning system which is connected and attached via said coupling to the magnetic field assembly.

8. The portable NMR device of claim 7, wherein the analysis modulus is further configured to compare, based on the carried out NMR measurements that are received by the analysis module, the first and second detections of the at least one contaminant and to subsequently determine, based on the comparison, an indication of oil cleanliness by using a lack of difference between the first and second detections as the indication of oil cleanliness.

9. A method of detecting an oil concentration in water, the method comprising:

generating with a portable nuclear magnetic resonance (NMR) device, containing at least one magnetic field source a magnetic field within a measurement volume in order to enable an on-line and in-line detection of an oil concentration in water that passes through the portable NMR device, when the oil concentration in the water is at least 50 parts per million (ppm);

carrying out nuclear magnetic resonance (NMR) measurements on the water in order to detect the oil concentration in the water with the portable NMR device;

determining via an analysis based on the carried out and obtained NMR measurements, that is performed by and with a computer processor of the portable NMR device, a measurement of the oil concentration in the water; and shielding an environment external to the measurement volume of the portable NMR device in order to substantially eliminate a magnetic fringe field from extending beyond an outer housing of the portable NMR device.

10. The method of claim 9, further comprising generating with the portable nuclear magnetic resonance (NMR) device, contained the at least one magnetic field source a magnetic field in order to enable a detection of at least one oil contaminant in the water that passes through the portable NMR device.

11. The method of claim 10, further comprising carrying out NMR measurements with the portable nuclear magnetic resonance device (NMR) device, containing the at least one magnetic field source in order to carry our the actual detection of the at least one oil contaminant in the water.

12. The method of claim 11, further comprising determining via the analysis performed by with a computer processor, based on the carried out and obtained NMR measurements, the determined concentration of the at least one oil contaminant that was detected in the water.

13. The method of claim 12, further comprising based on the determined concentration indicating, with the computer processor of the portable nuclear magnetic resonance (NMR) device that performs the analysis of the at least one oil contaminant in the water that passes through the portable NMR device, and subsequently providing as a result an indication of an amount of oil cleanliness within the water that passes through the portable NMR device.

* * * * *